United States Patent
Lee

[11] Patent Number: 6,154,881
[45] Date of Patent: Dec. 5, 2000

[54] FACE PROTECTOR

[76] Inventor: Yhan G. Lee, 5676 Broadway, Bronx, N.Y. 10463

[21] Appl. No.: 09/401,223
[22] Filed: Sep. 22, 1999
[51] Int. Cl.[7] .................................................. A61F 9/04
[52] U.S. Cl. ............................................................ 2/9
[58] Field of Search .................................. 2/8, 9, 11, 15, 2/10, 452, 206

[56] References Cited

U.S. PATENT DOCUMENTS

| | | |
|---|---|---|
| 2,360,101 | 10/1944 | Bowers ............................................ 2/8 |
| 2,798,222 | 7/1957 | Evans et al. ..................................... 2/9 |
| 3,060,444 | 10/1962 | Hoffmaster et al. ............................. 2/8 |
| 3,079,609 | 3/1963 | Hoffmaster ...................................... 2/8 |
| 4,040,123 | 8/1977 | Williams ........................................ 2/10 |
| 4,071,912 | 2/1978 | Budmiger ........................................ 2/8 |
| 4,464,800 | 8/1984 | Edwards ........................................ 2/452 |
| 4,853,974 | 8/1989 | Olim ............................................... 2/9 |
| 5,337,419 | 8/1994 | Russell ............................................ 2/9 |
| 5,365,615 | 11/1994 | Piszkin ........................................ 2/422 |
| 5,379,463 | 1/1995 | Schleger et al. ............................. 2/431 |
| 5,619,749 | 4/1997 | Banuchi .......................................... 2/9 |

Primary Examiner—Michael A. Neas
Attorney, Agent, or Firm—Richard L. Miller

[57] ABSTRACT

An improved face protector of a type having a head-engaging strap, a forehead engaging-stiffening member, a facing protecting-lens, and pivoting apparatus. The improvement includes the pivoting apparatus including a pair of studs that extend outwardly through associated pivoting-throughbores in the head-engaging strap, outwardly through associated pivoting-throughbores in the forehead engaging-stiffening member, and outwardly through associated pivoting-throughbores in the facing protecting-lens, and a pair of flat-head screws threadably engaging in the associated shafts of the studs from a direction of the facing protecting-lens and having heads disposed adjacent to the facing protecting-lens for setting friction level of the pivoting apparatus. The shafts of the studs have flats along a portion of their lengths extending from ends thereof so as to form flat portions having D-shaped lateral profiles. A pair of bushings being O-shaped and having D-shaped central throughbores fixedly receive the associated flat portions of the shafts of the studs and are disposed between and abut against the facing protecting-lens and the associated heads of the flat-head screws so as to prevent the studs from rotating and loosening each time the face protecting-lens is moved.

9 Claims, 2 Drawing Sheets

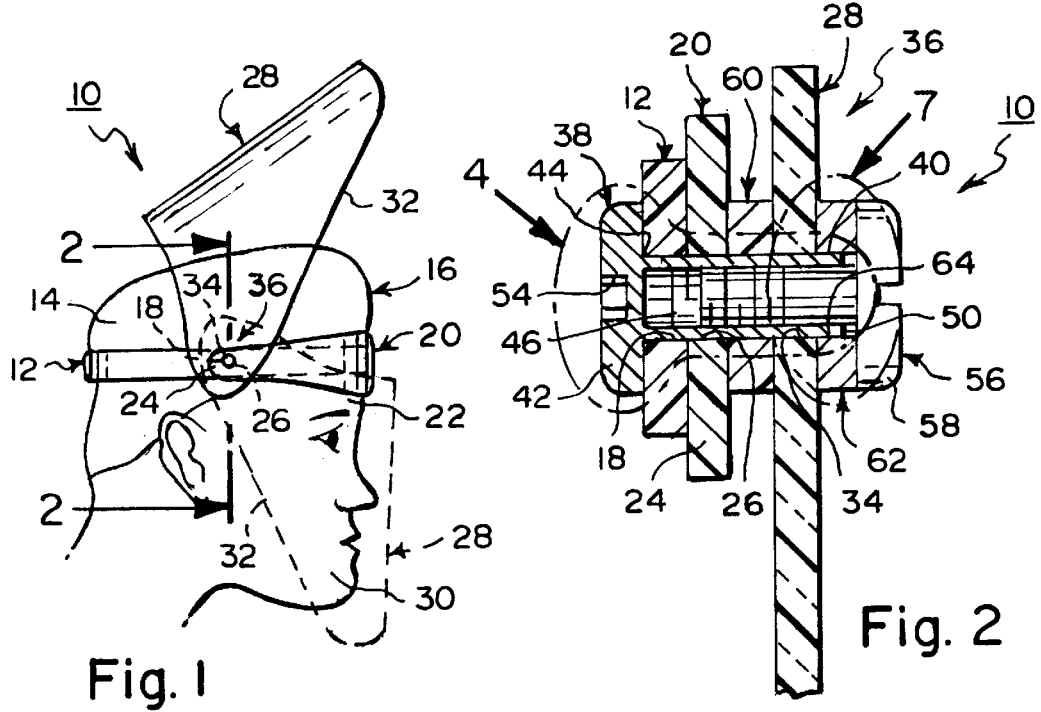
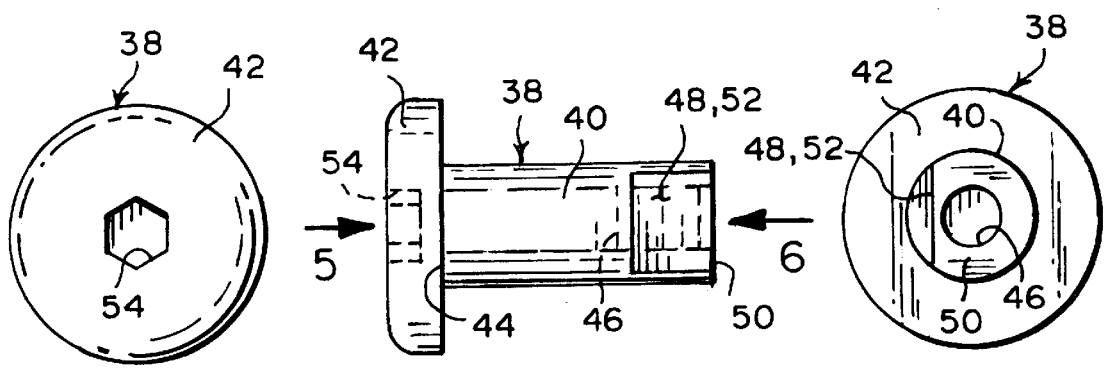
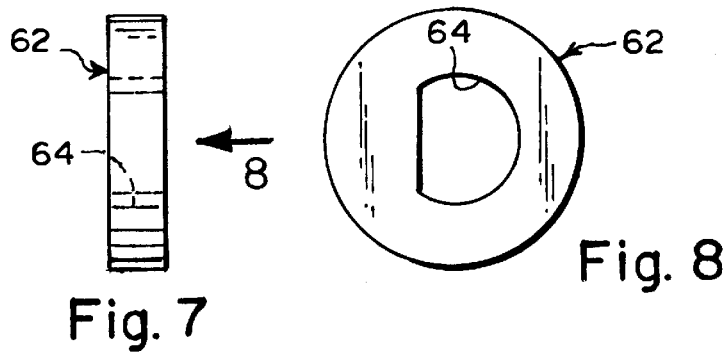

FACE PROTECTOR

BACKGROUND OF THE INVENTION

1. Field of the Invention

The present invention relates to a face protector. More particularly, the present invention relates to an improved face protector.

2. Description of the Prior Art

If the ozone layer is destroyed even partially, UVR strikes the face directly. UVR can cause wrinkles, freckles, sunburn, or even destroy melanin.

There are many types of creams for UVR, but they are not effective or easy to use. UV rays can be blocked by wearing a hat. Hats, however, cannot protect completely from UVR because of the angle of the sun.

Numerous innovations for face protectors have been provided in the prior art that will be described. Even though these innovations may be suitable for the specific individual purposes to which they address, however, they differ from the present invention.

A FIRST EXAMPLE, U.S. Pat. No. 4,071,912 to Budmiger teaches a welder's mask that has a lens at least part of which is formed of an infrared filter, an ultraviolet filter, a polarizer, an analyzer, and an optoelectric element between the polarizer and analyzer. The optoelectric element may be a ceramic crystal or fluid crystal that is electrically energizable by means of automatic circuitry connected to an UV-sensitive photocell to rotate the polarization plane of light coming from the polarizer to the analyzer in order automatically to darken the lens when exposed to a welding flame or arc.

A SECOND EXAMPLE, U.S. Pat. No. 4,853,974 to Olim teaches a face protector that comprises a flexible headband and a transparent flexible shield of sufficient size to protect the face of the wearer. The shield is sufficiently flexible and easily deformable so as to adapt to the shape of a user's head. Fastener means carried by the headband reusably and deftly attaching the band around the head of the wearer and also reusably and deftly attaching the headband to the shield. The fastener means on the headband are attached to lateral positions on the headband, and the fastener means on the shield are detachably suspended from the fastener means on the headband at these positions.

A THIRD EXAMPLE, U.S. Pat. No. 5,337,419 to Russell teaches a face protector for shielding the face of the wearer while permitting observation and pivoting of the shield toward and away from the face comprising: an elongated flexible band of absorbant padding sized and adapted to, be fitted about the forehead; a first elongated flexible stiffening member attached therealong to a corresponding confronting portion of the band; a second elongated stiffening member having a length greater than the first stiffening member and pivotally attached to the first stiffening member at corresponding end portions of the stiffening members so that the stiffening members are spaced apart when the band is fitted about the head; a flexible transparent face shield with an integral anti-glare, anti-fog coating connected at a top portion thereof to the second stiffening member along its length whereby pivotal movement of the second stiffening member relative to the first stiffening member permits movement of the shield toward and away from the face; and, a void provided in one end portion of the second stiffening member for accepting the corresponding end portion of the first stiffening member, thereby limiting the pivoting movement of the second stiffening member relative to the first stiffening member and the shield toward the face.

A FOURTH EXAMPLE, U.S. Pat. No. 5,365,615 to Piszkin teaches an aerodynamically configured face-shield suitable for sports-helmets or other similar head protective gear, which is inexpensively die-cut and readily conforming to the frontal vertical-brim region of an existing visorless-helmet via special mounting elements. The vestigial low-profile mounting-elements are non-intrusive, and permanently install via double-face mounting-tape, as extruded-plastic strips having elongated-bifurcations which are manually swedged into corresponding die-cut attachment-slots at opposite lateral sides of the helmet brim. Thus attached, the special faceshield is held rigidly in position against physical forces such as are encountered during bicycling; yet, may be instantly avulsedly detached by the user merely pulling the faceshield away from the brim mount-strips. This unique mounting methodology virtually eliminates potentially injurious fasteners heretofore employed in faceshield hardware design; plus, it presents an aerodynamically superior conformation.

A FIFTH EXAMPLE, U.S. Pat. No. 5,379,463 to Schleger et al. teaches facial protective wear including a facial shield member having a substantially transparent portion for allowing visible light to pass to the wearer's eyes and a support coupled to the facial shield for supporting the facial shield on the wearer's head. The facial shield member further has a nose protective portion extending over and protecting substantially the wearer's entire nose from in front of and from above and preferably has side portions protecting the wearer's eyes in a direction from the sides of the wearer's head. The facial shield member transparent portion preferably substantially prevents ultraviolet solar radiation from reaching the wearer's eyes and facial features, such as the nose and cheeks, and also from reaching the eyes in a direction from the sides of the head. The facial protective wear also can be used to protect the wearer from the wind and from injury due to flying objects. Various embodiments are described, including embodiment that clip onto existing eyewear or headwear. The nose protective portion can be made integrally with the transparent shield portion or removable.

A SIXTH EXAMPLE, U.S. Pat. No. 5,619,749 to Banuchi teaches an antiphotoaging face mask including a pair of sunglasses comprising a front frame member and pair of temples extending therefrom. The antiphotoaging face mask includes a flexible plastic wrap secured to the pair of sunglasses, the wrap including a front portion that extends over the nose of the wearer, as well as lateral side portions to cover at least lateral aspects of the head of the wearer. The flexible plastic wrap includes a layer of transparent plastic material that blocks at least harmful UV rays.

It is apparent that numerous innovations for face protectors have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide an improved face protector that avoids the disadvantages of the prior art.

ANOTHER OBJECT of the present invention is to provide an improved face protector that is simple and inexpensive to manufacture.

STILL ANOTHER OBJECT of the present invention is to provide an improved face protector that is simple to use.

BRIEFLY STATED, YET ANOTHER OBJECT of the present invention is to provide an improved face protector of a type having a head-engaging strap, a forehead engaging-stiffening member, a facing protecting-lens, and pivoting apparatus. The improvement includes the pivoting apparatus including a pair of studs that extend outwardly through associated pivoting-throughbores in the head-engaging strap, outwardly through associated pivoting-throughbores in the forehead engaging-stiffening member, and outwardly through associated pivoting-throughbores in the facing protecting-lens, and a pair of flat-head screws threadably engaging in the associated shafts of the studs from a direction of the facing protecting-lens and having heads disposed adjacent to the facing protecting-lens for setting friction level of the pivoting apparatus. The shafts of the studs have flats along a portion of their lengths extending from ends thereof so as to form flat portions having D-shaped lateral profiles. A pair of bushings being O-shaped and having D-shaped central throughbores fixedly receive the associated flat portions of the shafts of the studs and are disposed between and abut against the facing protecting-lens and the associated heads of the flat-head screws so as to prevent the studs from rotating and loosening each time the face protecting-lens is moved.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures on the drawing are briefly described as follows:

FIG. 1 is a diagrammatic side elevational view of the present invention in use;

FIG. 2 is an enlarged diagrammatic cross sectional view taken on line 2—2 in FIG. 1 of the present invention;

FIG. 4 is an enlarged diagrammatic side elevational view of the area generally enclosed by the dotted curve identified by arrow 4 in FIGS. 2 and 3 of the stud of the prevent invention;

FIG. 5 is a diagrammatic top plan view taken generally in the direction of arrow 5 in FIG. 4 of the head of the stud;

FIG. 6 is a diagrammatic bottom plan view taken generally in the direction of arrow 6 in FIG. 4;

FIG. 7 is an enlarged diagrammatic side elevational view of the area generally enclosed by the dotted curve identified by arrow 7 in FIGS. 2 and 3 of the locking bushing of the present invention; and FIG. 8 is a diagrammatic top plan view taken generally in the direction of arrow 8 in FIG. 7.

Figure 3:
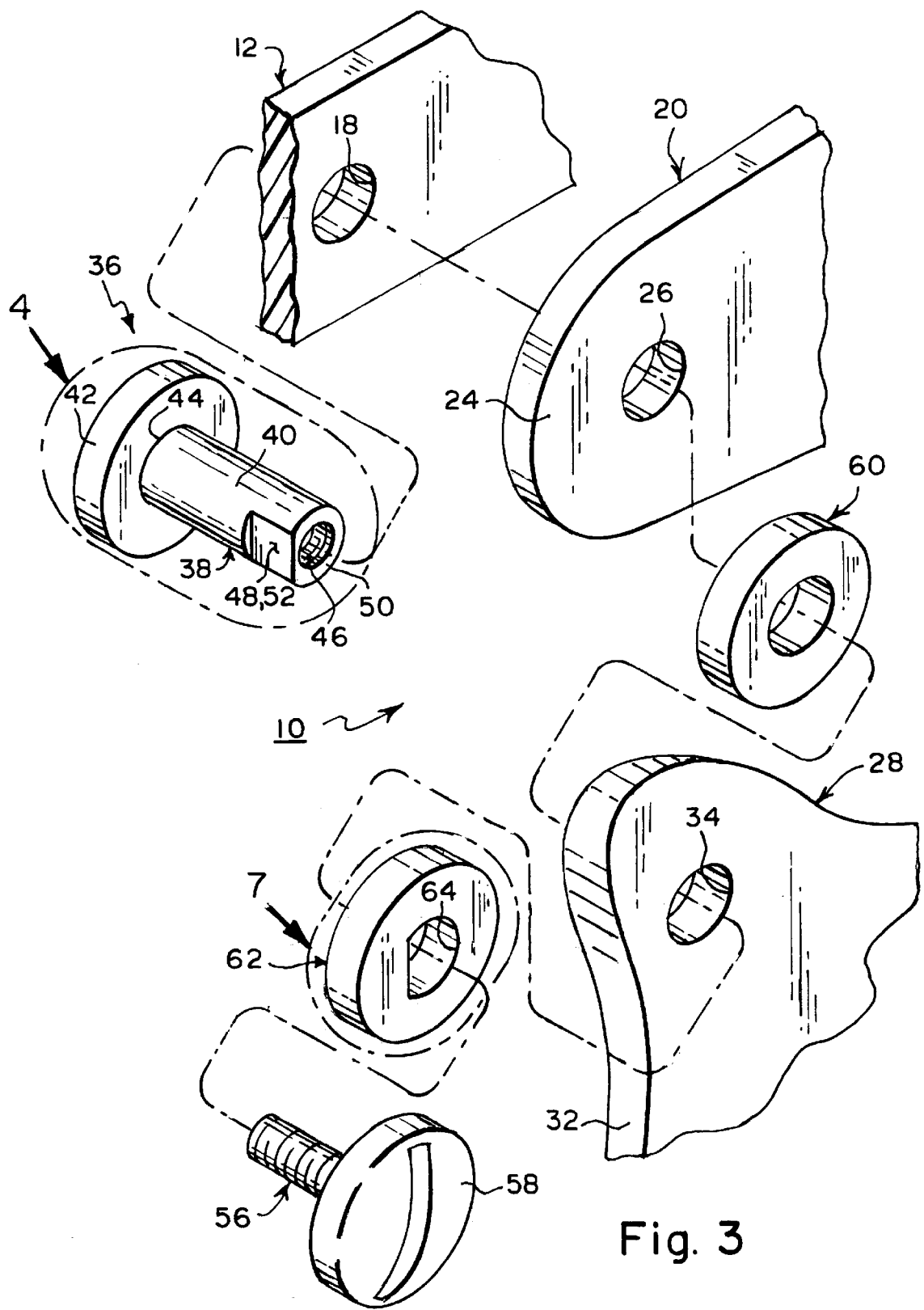
FIG. 3 is an exploded diagrammatic perspective view of FIG. 2.

LIST OF REFERENCE NUMERALS UTILIZED IN THE DRAWING 10 improved face protector of the present invention
12 head-engaging strap for encircling and engaging head 14 of wearer 16
14 head of wearer 16
16 wearer
18 pair of diametrically opposing pivoting-throughbores 18 in head-engaging strap 12
20 forehead engaging-stiffening member for overlying forehead 22 of wearer 16
22 forehead of wearer 16
24 pair of ends of forehead engaging-stiffening member 20
26 pivoting-throughbore in each end of pair of ends 24 of forehead engaging-stiffening member 20
28 facing protecting-lens for selectively covering face 30 of wearer 16
30 face of wearer 16
32 pair of terminal axial edges of facing protecting-lens 28
34 pivoting throughbore in each terminal axial edge of pair of terminal axial edges 32 of facing protecting-lens 28
36 pivoting apparatus
38 pair of studs of pivoting apparatus 36
40 shaft of each stud of pair of studs 38 of pivoting apparatus 36
42 flat head of each stud of pair of studs 38 of pivoting apparatus 36
44 one end of shaft of each stud of pair of studs 38 of pivoting apparatus 36
46 internal threads running axially in shaft of each stud of pair of studs 38 of pivoting apparatus 36
48 flat of shaft of each stud of pair of studs 38 of pivoting apparatus 36
50 other end of shaft of each stud of pair of studs 38 of pivoting apparatus 36
52 flat portion of shaft of each stud of pair of studs 38 of pivoting apparatus 36
54 hexagonally-shaped blindbore in flat head 42 of each stud of pair of studs 38 of pivoting apparatus 36 for receiving an Allen key (not shown) for turning stud of pair of studs 38 of pivoting apparatus 36
56 flat-head screw of pivoting apparatus 36
58 head of flat-head screw 56 of pivoting apparatus 36 for setting friction level of pivoting apparatus 36
60 first bushing of pivoting apparatus 36
62 second bushing of pivoting apparatus 36
64 D-shaped central throughbore in second bushing 62 of pivoting apparatus 36

DETAILED DESCRIPTION OF THE PREFERRED EMBODIMENT

Referring now to the figures, in which like numerals indicate like part, and particularly to FIG. 1, the improved face protector of the present invention is shown generally at 10 and is of a type having a head-engaging strap 12 for encircling and engaging the head 14 of a wearer 16 and having a pair of diametrically opposing pivoting-throughbores 18, a forehead engaging-stiffening member 20 extending along the head-engaging strap 12 for overlying the forehead 22 of the wearer 16 and having a pair of ends 24, wherein each end 24 has a pivoting-throughbore 26, a facing protecting-lens 28 pivotally attached to the forehead engaging-stiffening member 20 for selectively covering the face 30 of the wearer 16 and having a pair of terminal axial edges 32, wherein each terminal axial edge 32 has a pivoting-throughbore 34, and pivoting apparatus 36 pivotally attaching the face protecting-lens 28 to the forehead engaging-stiffening member 20 so as to allow the face protecting-lens 28 to pivot down onto the face 30 of the wearer 16 when in use and to pivot up off the face 30 of the wearer 16 when not in use.

The improvement can best be seen in FIGS. 2–8, and as such, will be discussed with reference thereto.

The improvement comprises the pivoting apparatus 36 comprising a pair of studs 38. Each stud 38 extends outwardly through an associated pivoting-throughbore 18 in the head-engaging strap 12, outwardly through an associated pivoting-throughbore 26 in the forehead engaging-stiffening member 20, and outwardly through an associated pivoting-throughbore 34 in the facing protecting-lens 28.

The improvement further comprises each stud 38 having a shaft 40 with a length extending outwardly through the associated pivoting-throughbore 18 in the head-engaging strap 12, outwardly through the associated pivoting-throughbore 26 in the forehead engaging-stiffening member 20, and outwardly through the associated pivoting-throughbore 34 in the facing protecting-lens 28.

The improvement further comprises each stud 38 having a flat head 42 disposed at one end 44 of the shaft 40 and abutting against the head-engaging strap 12.

The improvement further comprises the shaft 40 of the stud 38 being tubular with internal threads 46 running axially therein.

The improvement further comprises the shaft 40 of the stud 38 having a flat 48 along a portion of its length extending from the other end 50 thereof so as to form a flat portion 52 having a D-shaped lateral profile.

The improvement further comprises the flat head 42 of the stud 38 having an hexagonally-shaped blindbore 54 extending therein in line with and opposite to the shaft 40 for receiving an Allen key (not shown) for turning the stud 38.

The improvement further comprises a flat-head screw 56 threadably engaging in the shaft 40 of the stud 38 from a direction of the facing protecting-lens 30 and having a head 58 disposed adjacent to the facing protecting-lens 30 for setting friction level of the pivoting apparatus 36.

The improvement further comprises a first bushing 60 being O-shaped and receiving the shaft 40 of the stud 38 and being disposed between and abutting against the forehead engaging-stiffening member 20 and the facing protecting-lens 28.

The improvement further comprises a second bushing 62 being O-shaped and having a D-shaped central throughbore 64 fixedly receiving the flat portion 52 of the shaft 40 of the stud 38 and being disposed between and abutting against the facing protecting-lens 28 and the head 58 of the flat-head screw 56 so as to prevent the stud 38 from rotating and loosening each time the face protecting-lens 28 is moved.

The improvement further comprises the face protecting-lens 28 being polycarbonate for filtering out ultraviolet radiation.

It will be understood that each of the elements described above, or two or more together, may also find a useful application in other types of constructions differing from the types described above.

While the invention has been illustrated and described as embodied in an improved face protector, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An improved face protector of a type having a head-engaging strap for encircling and engaging the head of a wearer and having a pair of diametrically opposing pivoting-throughbores, a forehead engaging-stiffening member extending along the head-engaging strap for overlying the forehead of the wearer and having a pair of ends, wherein each end has a pivoting-throughbore, a facing protecting-lens pivotally attached to the forehead engaging-stiffening member for selectively covering the face of the wearer and having a pair of terminal axial edges, wherein each terminal axial edge has a pivoting-throughbore, and pivoting apparatus pivotally attaching the face protecting-lens to the forehead engaging-stiffening member so as to allow the face protecting-lens to pivot down onto the face of the wearer when in use and to pivot up off the face of the wearer when not in use, said improvement comprising the pivoting apparatus comprising a pair of studs; each stud extending outwardly through an associated pivoting-throughbore in the head-engaging strap, outwardly through an associated pivoting-throughbore in the forehead engaging-stiffening member, and outwardly through an associated pivoting-throughbore in the facing protecting-lens.

2. The protector as defined in claim 1, wherein said improvement further comprises each said stud having:
   a) a shaft with a length extending outwardly through said associated pivoting-throughbore in the head-engaging strap, outwardly through said associated pivoting-throughbore in the forehead engaging-stiffening member, and outwardly through said associated pivoting-throughbore in the facing protecting-lens; and
   b) a flat head disposed at one end of said shaft and abutting against the head-engaging strap.

3. The protector as defined in claim 2, wherein said improvement further comprises said shaft of said stud being tubular with internal threads running axially therein.

4. The protector as defined in claim 2, wherein said improvement further comprises said shaft of said stud having a flat along a portion of its length extending from the other end thereof so as to form a flat portion having a D-shaped lateral profile.

5. The protector as defined in claim 2, wherein said improvement further comprises said flat head of said stud having an hexagonally-shaped blindbore extending therein in line with and opposite to said shaft for receiving an Allen key for turning said stud.

6. The protector as defined in claim 4, wherein said improvement further comprises a flat-head screw threadably engaging in said shaft of said stud from a direction of the facing protecting-lens and having a head disposed adjacent to the facing protecting-lens for setting friction level of the pivoting apparatus.

7. The protector as defined in claim 2, wherein said improvement further comprises a first bushing being O-shaped and receiving said shaft of said stud and being disposed between and abutting against the forehead engaging-stiffening member and the facing protecting-lens.

8. The protector as defined in claim 6, wherein said improvement further comprises a second bushing being O-shaped and having a D-shaped central throughbore fixedly receiving said flat portion of said shaft of said stud and being disposed between and abutting against the facing protecting-lens and said head of said flat-head screw so as to prevent said stud from rotating and loosening each time the face protecting-lens is moved.

9. The protector as defined in claim 1, wherein said improvement further comprises the face protecting-lens being polycarbonate for filtering out ultraviolet radiation.

* * * * *